United States Patent [19]
Falconer

[11] Patent Number: 6,152,903
[45] Date of Patent: *Nov. 28, 2000

[54] MEDICAL OR SURGICAL APPLIANCE, IN PARTICULAR A URINE COLLECTION DEVICE

[75] Inventor: Malcolm Ian Falconer, Wandsworth, United Kingdom

[73] Assignee: Bristol-Myers Squibb Company, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/835,288

[22] Filed: Apr. 9, 1997

[30] Foreign Application Priority Data

Apr. 9, 1996 [GB] United Kingdom ............. 9607271
Mar. 24, 1997 [GB] United Kingdom ............. 9706076

[51] Int. Cl.[7] .................................................. A61F 55/44
[52] U.S. Cl. ......................... 604/351; 604/317; 604/353
[58] Field of Search ..................... 604/323, 345–353, 604/342, 179; 128/DIG. 26

[56] References Cited

U.S. PATENT DOCUMENTS

| | | | |
|---|---|---|---|
| 2,883,985 | 4/1959 | Evans | 604/350 |
| 3,357,430 | 12/1967 | Rosenberg | 604/353 |
| 3,405,714 | 10/1968 | Moss | 604/350 |
| 3,765,421 | 10/1973 | Poprik | 641/179 |
| 4,445,894 | 5/1984 | Kovacs | 604/179 |
| 4,671,787 | 6/1987 | Widman | 604/179 |
| 4,813,943 | 3/1989 | Smith | 604/353 |
| 5,193,553 | 3/1993 | Kalinoski | 604/353 |
| 5,386,802 | 2/1995 | Hang-Fu | 604/342 |
| 5,478,334 | 12/1995 | Bernstein | 604/345 |
| 5,496,282 | 3/1996 | Militzer et al. | 604/179 |
| 5,672,159 | 9/1997 | Worrick | 128/DIG. 26 |

FOREIGN PATENT DOCUMENTS 161047 11/1985 European Pat. Off. ............. 604/353

Primary Examiner—Mark O. Polutta
Attorney, Agent, or Firm—Stuart E. Krieger

[57] ABSTRACT

A urine collection device, a band for retaining the device and a method for attaching a medical device to the wearer's body. A band has two tabs. Each tab has one end attached to the band and a free end for extending through a hole in the device and attaching to the band. The band with the device mounted to it can be retained on the wearer's body.

11 Claims, 4 Drawing Sheets

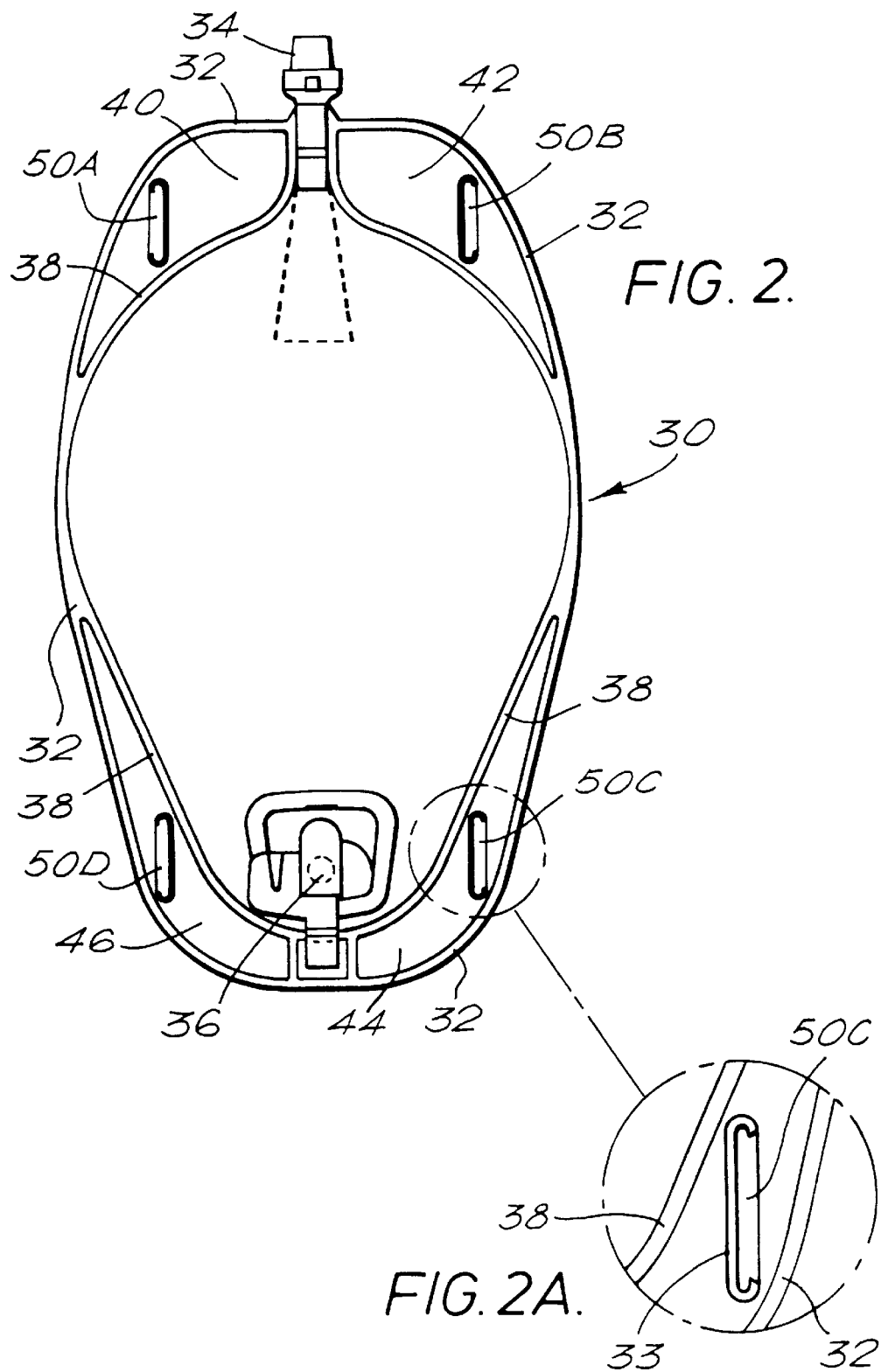

MEDICAL OR SURGICAL APPLIANCE, IN
PARTICULAR A URINE COLLECTION
DEVICE

BACKGROUND OF THE INVENTION

Urine collection devices are known, as are other medical or surgical appliances which are worn on the body. One example is illustrated in our U.K. Patent Application No. 2,296,665. The present invention aims to provide an appliance, e.g. a urine collection device of high capacity, which is particularly comfortable to wear and yet easy to attach and remove.

In PCT Application No. WO96/06646 there is disclosed a coupling device for a leg urinal. A leg bag has straps, one end of each strap is provided with loop material and the other end with hook material. The straps can be wrapped around the leg and easily connected together at a comfortable tension as determined by the patient. This arrangement has no positive way of ensuring that the bag is prevented from shifting its position relative to of the strap.

In U.K. Patent Application No. 2,215,211A there is shown a urine bag (1) made of two flexible sheets (10,11) welded together at their edges and along two vertical lines (16,17) to divide the bag into three vertical chambers (18 to 20). Two pairs of mounting apertures (21, 22, 23 and 24) receive respective straps (2 and 3) by which the bag is secured around the leg (4). The straps (2 and 3) pass behind the bag (1) between the bag and the leg where they have portions (32) of increased width that are stiffened by folding back at their ends (33 and 34). A part (35) of each strap (2 and 3) is elastic and they have press-to-close loop and hook fabric fasteners. The portions (32) of greater width limit the extent by which the edges of the bag can slide together along the strap as the bag fills with urine, thereby reducing bunching. However, if it is desired to remove this design of bag from the leg, it is necessary either to withdraw a considerable length of strap through the apertures (21 and 22, or 23 and 24), which is time consuming and awkward for elderly or infirm wearers, or to strip apart the strap ends. This stripping apart causes a situation wherein, briefly, the mounting of the bag on the leg is insecure. If the bag is full, this will cause apprehension to elderly or infirm persons. It is an aim of the present invention to provide an improved arrangement.

SUMMARY OF THE INVENTION

According to one aspect of the invention, there is provided a method of attaching a medical or surgical appliance to a part of the body of the wearer of the appliance, including providing a pair of slots or holes in the appliance, providing a band of fabric material of a first kind which has a pair of tabs permanently fixed thereon, at equal spacing to the holes or slots, each tab being of a fabric material of a second kind, threading the band through said holes or slots, and releasably securing each tab to the band in face-to-face manner.

In an advantageous embodiment of the invention, the material of the first kind is a fabric having loops on one of its surfaces and the material of the second kind is a fabric having hooks on one of its surfaces.

In use, the band extends around the relevant body part of the wearer and holds the appliance onto it, once the tab is closed onto the band.

According to another aspect of the invention, there is provided a medical or surgical appliance having two holes or slots therein through each of which a band can be threaded, first and second tabs each permanently attached to the band, and a fabric of a first kind on at least one surface of the band and a fabric of a second kind on at least one surface of each tab, the tabs being located on the band such that the distance between them is substantially equal to the distance between the holes or slots, and the tabs being connected to the band and arranged so that the band can be manipulated to fasten together said surfaces in face-to-face arrangement and thereby hold the appliance onto the band.

According to a further aspect of the invention, there is provided a medical or surgical appliance suitable for attachment to the leg of a wearer, the appliance comprising a bag and an attachment means, the bag having two pairs of zones which are defined by plastics welds and which are sealed against ingress of liquid, each of these zones being provided with a through slot which is substantially vertical when the bag is being worn on a wearer who is in a normal upright position; and the attachment means comprising at least a pair of bands, one such band having a first and second tab thereon permantently attached thereto at a mutual spacing substantially equal to the spacing between the slots of one pair of zones, and the other such band having a first and a second tab thereon permanently attached thereto at a mutual spacing substantially equal to the spacing of the slots of the other pair of zones; each of said tabs having either a fabric of a first kind or a fabric of a second kind or a fabric of a first kind on a surface which in use confronts the tab whereby these surfaces can be manipulated to fasten together in face-to-face arrangement.

In a preferred embodiment, upper and lower bands may be provided. Desirably the upper band is wider than the lower band.

According to a preferred embodiment the present invention, there is provided a urine collection device in which a bag, optionally pleated, for receiving urine is secured in known manner to a pubic attachment plate, has at least two slots in non-liquid containing regions of the bag, and is connected to a leg band via a pair of tabs, the tabs having surfaces which carry hooks or loops and the band having a surface which carries loops or hooks as the case may be, whereby interengagement between the hooks and loops of the respective surfaces holds the bag to the band and hence to the wearer.

BRIEF DESCRIPTION OF THE DRAWINGS

FIG. 2 is a front elevational view of a urine collection device, in accordance with the present invention;

FIG. 2A is an enlarged view of the circled portion in FIG. 2;

DETAILED DESCRIPTION OF THE DRAWINGS

Figure 1A:
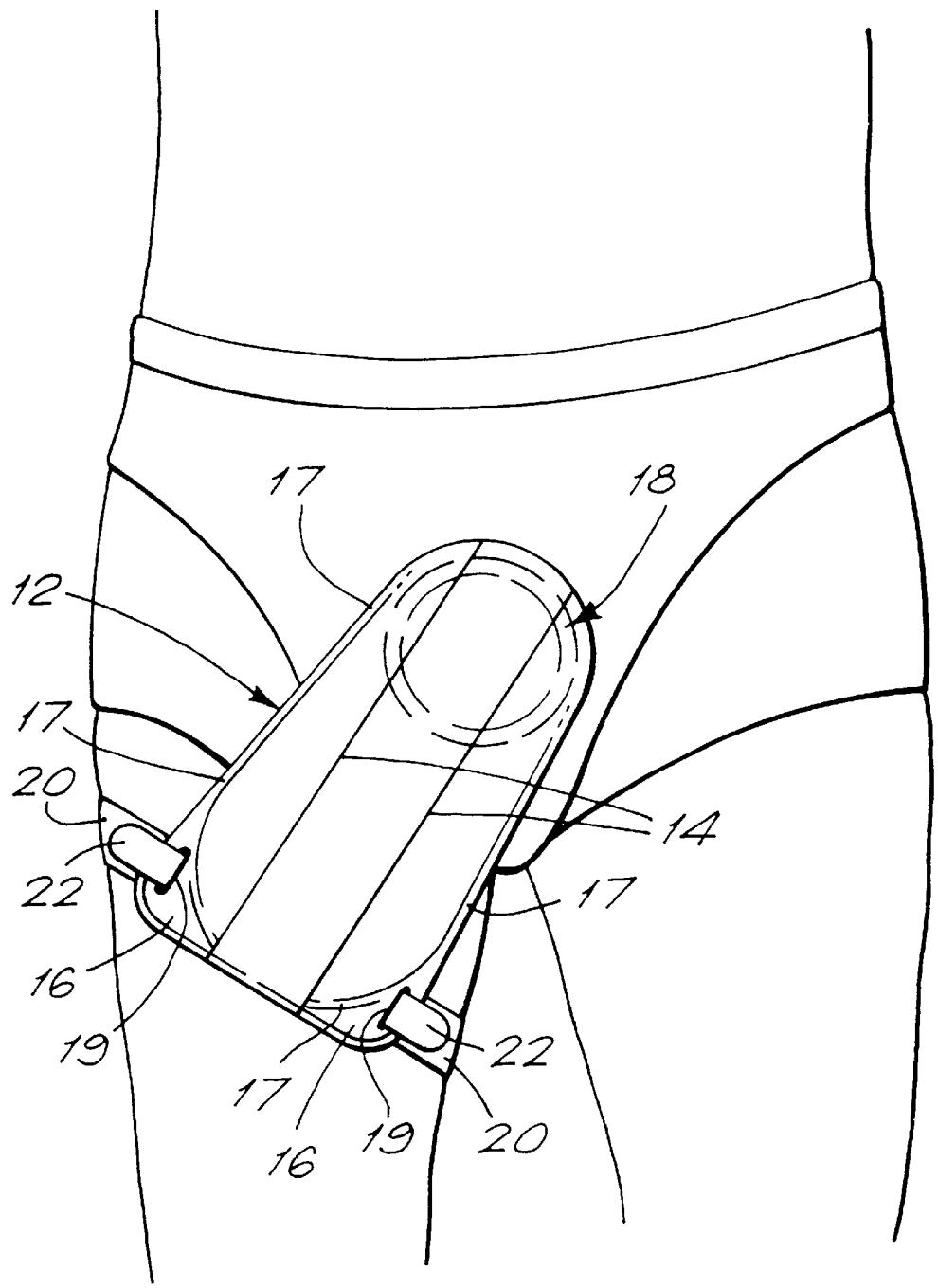
FIG. 1A is a perspective view of a urine collection device retained on a wearer's leg, in accordance with the present invention.

The urine collection device shown in FIG. 1A comprises a plastics bag 12 having front and rear walls and having pleats 14 in order to render it capable of carrying, if necessary, a substantial quantity of urine. The bag is made by superposing a pair of sheets which are then welded together by a plastics weld 17 which defines the liquid-containing volume of the bag. Areas 16 in the lower region of the bag are located outside the weld and contain slots 19 therethrough. The upper end of the bag is provided with a pubic pressure plate and fitting 18 so that the plate can be fitted to the wearer around his or her pubic area. For further information on how such a plate and fitting may be attached to the body of a male wearer, the reader is referred to U.K. Patent No. 2 233 232B. However, other forms of pubic fittingly may be employed.

A leg band 20 encircles the leg, of the wearer, this band being provided with a surface area having, fabric hooks. A pair of tabs 22 are provided, each having one of its ends permanently attached to the band 20. The tabs 22 have one of their surfaces provided with fabric loops. The loops and hooks referred to may be of the kind which are found in the well known fastening arrangement known under the Trade Mark VELCRO. The loops may be on the tabs and the hooks on the leg band, or the loops may be on the leg, band and the hooks on the tabs. In use, the tabs are pushed through the slots 19 and folded over as shown to engage with the confronting surface of the leg band. The spacing between the tabs is substantially equal to that between the holes or slots. Hence the bag 12 can be held smoothly spread out, and supported by the relevant limb of the wearer. It will be understood that in use the two tabs which may be "VELCRO" are pushed through the slots in the leg bag and fastened back onto the face of the band. The face of the band is made up of a loop type material which receives the hooks on the "Velcro" tabs. Once the tabs are fastened down the bag is held secure and is unable to bunch toward its centre. The bands are fastened to the leg and held in place by a tab (e.g. 69), see FIG. 3, as is commonplace in the art. Therefore, the bag is held in a safe, secure and comfortable manner while yet being readily released for removal if required. An arrangement of spaced slots in a bag together with equally spaced tabs on a band can be employed in various kinds of collection bag, e.g. a leg-bag arrangement of the kind shown in PCT Application No. WO96/06646.

Figure 1B:
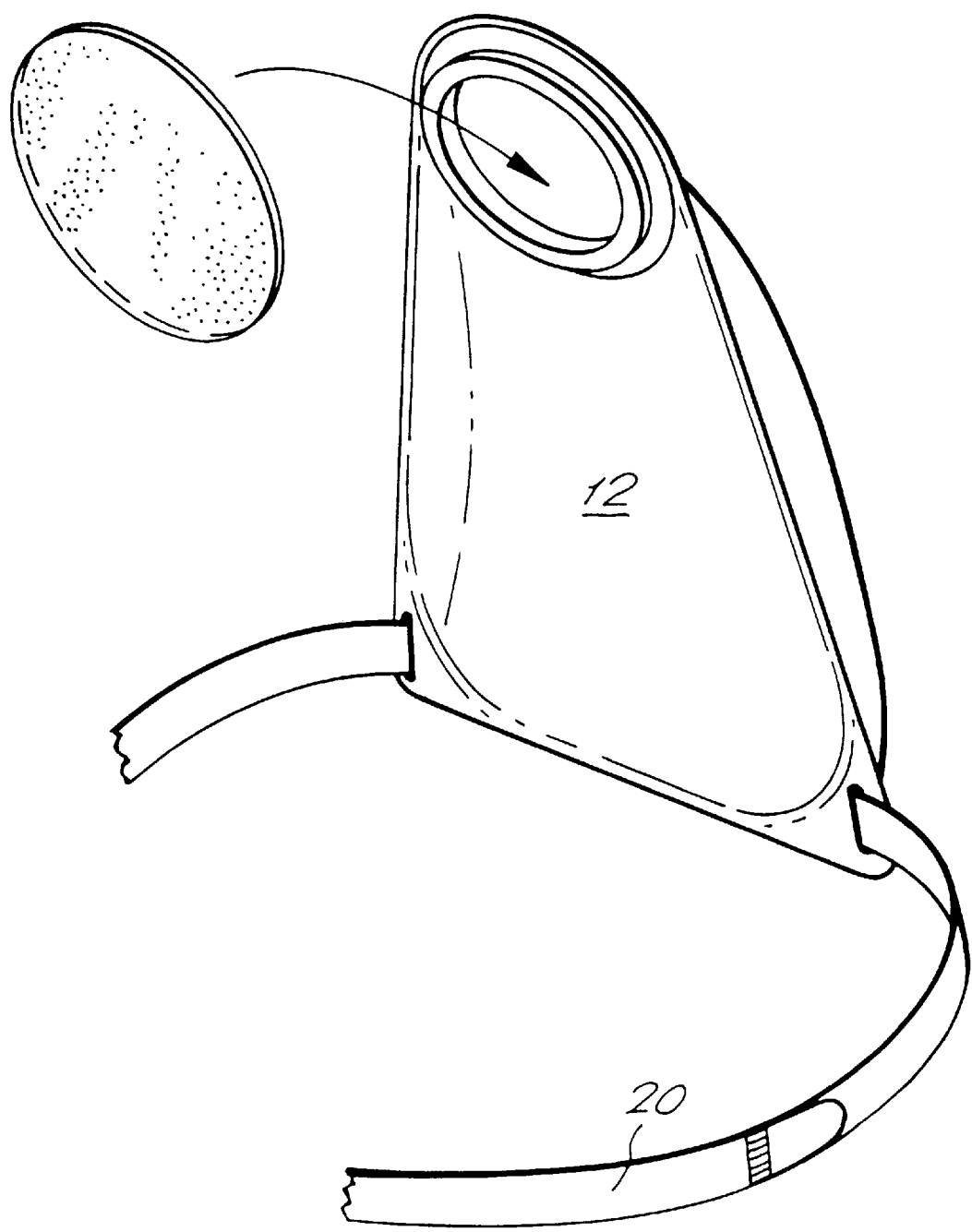
FIG. 1B is a perspective view of a urine collection device, in accordance with the present invention.

The urine collection device shown in FIG. 1B is similar, except that it does not have pleats. Its upper end is in use fixed to a pubic plate and fitting and its lower end is secured to a leg of the wearer by a band 20 which is similar to that described in connection with FIG. 1A. In FIG. 1B, the tabs are not visible.

Referring now to FIGS. 2 and 2A, these show a leg bag 30 forming part of the invention comprising a pair of plastics sheets welded together around the periphery by a weld seam 32. A tube connector 34 is welded into the top of the bag, through which urine enters. A drainage tap 36 welded to a lower portion of the bag allows urine to be emptied from the bag. The two plastics sheets are joined together by the weld seam 32 and the liquid-containing portion of the bag is defined by a second weld seam 38 which merges with the weld seam 32 at two opposed middle regions of the bag. It is seen that these two seams 32, 38 demarcate four zones 40, 42, 44, 46 of the bag from which liquid is excluded. Each such zone has a through slot 50. The slots 50 are substantially vertical when the appliance is in its normal upright position of use, as it would be if attached to the leg of a person standing upright. The plastics surrounding the slots is strengthened by a short weld as is more clearly illustrated at 33 in FIG. 2A. This is to prevent the bag film being inadvertently torn. Each of the slots 50A to 50D is dimensioned to receive a corresponding tab.

Figure 3:
FIG. 3 is a side-elevational view of a strip or band, in accordance with the present invention.
Figure 4:
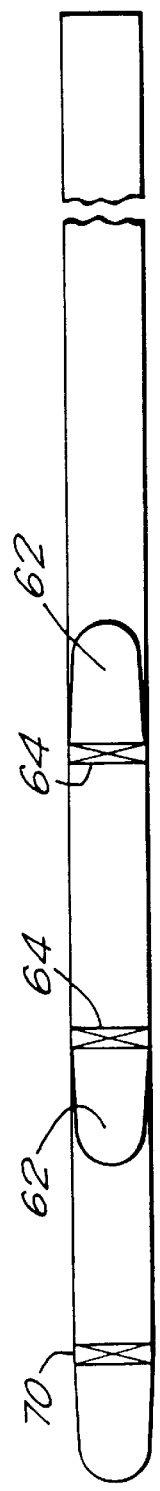
FIG. 4 is a top plan view of the strip or band of FIG. 3.

FIGS. 3 and 4 illustrate in cross-section and plan view respectively, one form of band usable in the present invention. The band 60 may be made of a nylon-rubber mixture and is manually extensible to a limited extent. A pair of tabs 62 are fixed to the band 60, e.g. by stitching as shown at 64, at locations along the band 60, the spacing between the stitched areas 64 being substantially equal to the spacing between a pair of slots 50A, 50B. As shown in the drawing, this spacing is substantially the same as the spacing between slots 50C and 50D but it would of course be different if the bag shape were such that it is wider (or narrower) at the bottom than at the top. The side 66 of the band has a loop-type fabric thereon and an end portion 68 of the band, stitched to the remainder of the band at 70, has hook-type fabric on its surface 69. This enables the ends to be joined as desired so that the bag 30 can be attached to a leg. The surfaces 62A have hook-type fabric theron.

Figure 5:
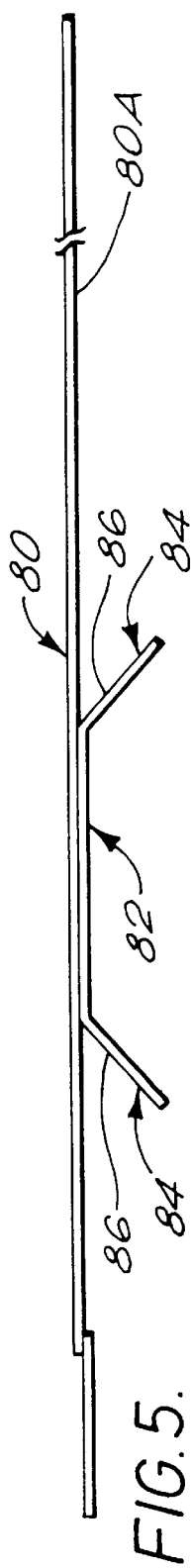
FIG. 5 is a side-elevational view of another embodiment of a strip or band, in accordance with the present invention.
Figure 6:
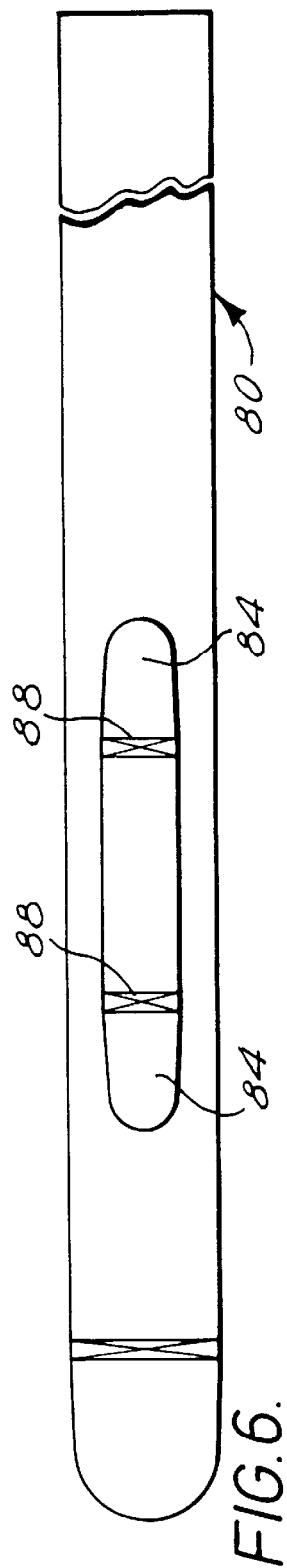
FIG. 6 is a top plan view of the strip or band of FIG. 5.

The construction of the band 80 shown in FIGS. 5 and 6 is generally similar to that shown in FIGS. 3 and 4 except that in the FIGS. 5 and 6 embodiment, instead of two tabs 62, a single strip of suitable material 82 is attached to the band 80; this has hook-type fabric 84 on the indicated portions 86 of the material. The side 80A of the band carries loop-type fabric. The material 82 is stitched to the band 80 at the region 88.

A system comprising a band which carries a pair of tabs fixed thereto, the tabs in their fastened position overlying the band and having either hooks or loops to cooperate with loops or hooks on the band can of course be employed to secure various kinds of medical or surgical appliance to the body of a wearer. For example a catheter or a wound protector could be supported by such an arrangement. The spacing of the tabs would be substantially equal to the spacing of slots provided in the appliance, so as to achieve the benefit of holding the appliance on the body without bunching or crumpling.

What is claimed is:

1. A urine collection device comprising:
   a bag having an opening for inletting urine, and a chamber for collecting the urine, said bag having two spaced apart retaining holes;
   a band having a contactable surface, said band having first and second tabs, each tab having an end attached to said band and a free end, said tabs being spaced apart and each tab having a length appropriate to extend through one of said retaining holes and contact said contactable surface, said free end having attachment means for removably attaching said free end to said contactable surface, said band having retaining means for retaining said band on a body portion of a wearer.

2. The urine collection device of claim 1 wherein said free end and contactable surface are removably attachable to each other with hooks and loops.

3. The urine collection device of claim 1 wherein the end of each of said tabs is affixed to said band.

4. The urine collection device of claim 1 wherein said bag is pleated.

5. The urine collection device of claim 1 wherein said bag is plastic and has a zone for each hole, said zones being leak proof.

6. The urine collection device of claim 1 wherein said strip has two ends that are fastenable together.

7. The urine collection device of claim 6 wherein the two ends include hook and loop elements.

8. The collection system of claim 1 wherein said band is an endless loop.

9. A method for attaching a medical appliance on a body portion of the wearer, comprising the steps of:

providing a medical appliance having two holes,
providing a band having a contactable surface and two tabs, said tabs having one end secured to the band and a free end extending therefrom;
extending said free end of each tab through one of said holes,
securing said free end to the contactable surface; and
securing said band around a portion of the wearer's body.

10. The method of claim 9 wherein the said step of securing said free end to the contactable surface includes fastening hook and loop elements together.

11. The method of claim 10 wherein said step of securing said band around a portion of the wearer's body includes fastening hook and loop elements together.

* * * * *